United States Patent [19]

Phillipps et al.

[11] 3,969,345

[45] July 13, 1976

[54] 20β,21-EPOXY-3α-HYDROXY-5α-PREGNANES AND DERIVATIVES THEREOF

[75] Inventors: Gordon Hanley Phillipps, Wembley; Christopher Earle Newall, London, both of England

[73] Assignee: Glaxo Laboratories Limited, Greenford, England

[22] Filed: Feb. 20, 1975

[21] Appl. No.: 551,315

Related U.S. Application Data

[62] Division of Ser. No. 208,961, Dec. 16, 1971, Pat. No. 3,882,151.

[30] Foreign Application Priority Data

Dec. 17, 1970 United Kingdom............... 60065/70

[52] U.S. Cl.................... 260/239.55 R; 260/397.45; 260/397.47; 424/243; 260/239.5

[51] Int. Cl.².............................................. C07J 5/00
[58] Field of Search........................... 260/239.55 R

[56] References Cited
UNITED STATES PATENTS 3,822,298   7/1974   Clayton et al. .................. 260/397.4

Primary Examiner—Elbert L. Roberts
Attorney, Agent, or Firm—Bacon & Thomas

[57] ABSTRACT

The invention provides 3α-oxygenated pregnane 21-ethers possessing a hydroxy group in the 3α-position; a hydrogen atom or a methyl group at the 10-position; a hydrogen atom in the 17α-position; a keto group in the 20-position; and an etherified hydroxyl group in the 21-position.

4 Claims, No Drawings

20β,21-EPOXY-3α-HYDROXY-5α-PREGNANES AND DERIVATIVES THEREOF

This application is a division of application Ser. No. 208,961, filed Dec. 16, 1971, and now U.S. Pat. No. 3,882,151.

This invention is concerned with improvements in or relating to compounds of the pregnane series having useful anaesthetic activity.

It has long been known that a number of steroids give rise to profound depression of the central nervous system and act pharmacodynamically as anaesthetics or hypnotics. Such compounds have been the subject of considerable study in an attempt to find anaesthetics to replace such substances as thiopentone sodium, normally used but well known to be accompanied by some degree of hazard and disadvantage. The literature shows that very many steroid compounds have been studied in this regard. Reviews and discussions of some of the work carried out are to be found, for example, in "Methods in Hormone Research" (Edited by Ralph I. Dorfman, Vol. III, Part A, Academic Press, London and New York, 1964, pages 415–475); H. Witzel, Z, Vitamin Hormon-Fermentforsch 1959, 10, 46–74; H. Selye, Endocrinology, 1942, 30, 437–453; S. K. Figdor et al., J. Pharmacol. Exptl. Therap., 1957, 119, 229–309 and Atkinson et al., J. Med. Chem. 1965, 8 426–432.

A thorough review of the literature indicates that anaesthetic steroids generally possess poor activity and/or long induction periods. With such compounds a variety of undesired side effects such as paraesthesia and vein damage have also been noted. Steroids possessing anaesthetic activity hitherto described are generally relatively simple pregnane derivatives, often hydroxylated in the 3-position, the general trend having been in the latter case to study 3β-hydroxy compounds rather than 3α-hydroxy compounds.

We have now found that certain new compounds of the pregnane series which possess inter alia a 3α-oxygenated-21-ether structure and which are more particularly described hereinafter have remarkable anaesthetic properties.

The aforesaid 3α-oxygenated pregnane 21-ethers may be generally characterized as being steroids of the pregnane series having anaesthetic properties and further characterized by possessing a hydroxy or acyloxy group in the α-configuration at the 3-position; an oxo group at the 20-position and preferably also at the 11-position; a hydrogen atom at the 17α-position; a keto group at the 20-position and an etherified hydroxy group at the 21-position.

The etherified hydroxy group at the 21-position is preferably a saturated or unsaturated aliphatic, cycloaliphatic, araliphatic, aromatic or heterocyclic hydrocarbyloxy group which may if desired, be substituted.

The expression "pregnane series" as used herein includes not only compounds of the conventional pregnane (5α or 5β, particularly the former) ring structure, if desired possessing unsaturation, but also the corresponding 19-nor compounds, the presence or absence of a methyl group at the 10-position having little influence on anaesthetic properties.

The above-defined 3α-oxygenated pregnane 21-ether anaesthetics have been found to induce anaesthesia with generally short induction periods, the anaesthetic action in general being at suitable doses virtually instantaneous; the compounds are thus excellent anaesthetics for inducing anaesthesia which is to be maintained e.g. by an inhalation anaesthetic such as ether, halothane, nitrous oxide, trichloroethylene etc. The compounds are however capable of maintaining anaesthesia and analgesia to a sufficient degree to enable various surgical operations to be conducted without the aid of an inhalation anaesthetic, the required degree of anaesthesia being maintained if necessary by repeated administration (or even continuous administration). Moreover, the said anaesthetics in accordance with the invention in general give rise to minimal side-effects compared to previously described steroidal anaesthetics.

Certain of the new compounds according to the invention may also serve as solubilisers for the anaesthetic steroid 3α-hydroxy-5α-pregnane-11,20-dione in analogous manner to the 21-acyloxy compounds described in our Belgian Patent No. 752,165. Thus we have found it possible to prepare solutions of 3α-hydroxy-5α-pregnane-11,20-dione, in for example aqueous solutions of parenterally acceptable surface active agents, having as solubility promoter 3α-hydroxy-21-propoxy-5α-pregnane-11,20-dione. In this manner the solubility of 3α-hydroxy-5α-pregnane-11,20-dione may be increased several-fold.

The invention further includes 3α-esters of the above-defined 3α-hydroxy-pregnane 21-ethers, particularly lower alkanoyl esters, for example, containing in the alkanoyl group up to 5 carbon atoms, e.g. the acetate. Such esters may also be esters containing one or more substituents in the alkanoyl portion e.g. halogen atoms, carboxy groups, amino groups, etc., or salts thereof when a substituent capable of forming a salt with an acid or a base is present. Generally the induction period of a 3-ester is longer than that with a corresponding 3α-hydroxy compound. Both the 3α-hydroxy compounds and the corresponding 3-esters may be regarded as central nervous system depressants and thus in suitable doses may also be used as hypnotics or sedatives.

The above defined 3α-hydroxy-21-ether-pregnane compounds and the corresponding 3α-esters are hereinafter collectively referred to as 3α-oxygenated-pregnane 21-ether anaesthetics.

The 3α-oxygenated-pregnane-21-ether anaesthetics may contain further substitution, for example at the 16-position. Examples of substituents which may be present at position 16 include either one or two alkyl groups, especially lower (e.g. having 1–6 carbon atoms) alkyl groups, for example methyl groups.

The compounds of the invention may also be substituted at the 2β-position for example by an acyloxy group containing for example 1–9 carbon atoms, an ether or thioether group (i.e. the residue of an alcohol, a phenol or a thiol) containing for example 1–9 carbon atoms (e.g. methoxy), an alkyl or cycloalkyl group for example containing up to 9 carbon atoms, an aryl group, (e.g. a phenyl group), an aralkyl group (e.g. a benzyl group), a hydroxy group, a thiocyanato group, a nitro-oxy group, or a halogen atom. Acyloxy substituents (which may be saturated or unsaturated) include lower ($C_1$–$C_6$) alkanoyloxy groups, (substituted if desired, for example, with one or more halogen, e.g. chlorine, atoms, lower alkoxy, amino or substituted amino groups), aroyloxy groups, e.g. a benzoyloxy group, or aralkanoyloxy groups, e.g. a phenylacetoxy group. Ether substituents, which may be saturated or unsaturated, include lower ($C_1$–$C_6$) alkoxy groups, lower alkenyloxy groups (e.g. an allyloxy group) cycloalkoxy groups, e.g. a cyclohexyloxy group, aryloxy groups, e.g. a phenoxy group, and aralkoxy groups, e.g. a benzyloxy group. Thioether groups corresponding to the above-mentioned ether groups are representative of 2β-thioether substituents.

The 2β-substituent may alternatively be an azido, sulphonyloxy (e.g. tosyloxy) group or an acylthio group.

Examples of 2β-alkyl groups include especially lower alkyl groups containing 1-5 carbon atoms such as methyl, ethyl, propyl, butyl, isobutyl and t-butyl groups. An example of a cycloalkyl group is a cyclohexyl group.

Examples of lower alkanoyloxy 2β-substituents include acetoxy, propionyloxy, butyryloxy groups, piperidinoacetoxy, morpholinoacetoxy, diethylaminoacetoxy and chloroacetoxy. Examples of lower alkoxy groups include methoxy, ethoxy, propoxy, isopropoxy n-butoxy and t-butoxy groups, and the corresponding thio compounds exemplify lower alkyl thio substituents.

Lower alkoxy and lower alkylthio substituents at the 2β-position may themselves be substituted for example by one or more halogen (e.g. chlorine) atoms, lower alkoxy, esterified carboxyl (e.g. ethoxycarbonyl), hydroxy, amino or substituted amino, e.g. morpholino groups, or substituted or unsubstituted acyloxy, e.g. morpholinoacetoxy, chloroacetoxy or diethylaminoacetoxy, or heterocyclic groups, e.g. a tetrahydrofuranyl group. Alkyl, cycloalkyl and aryl groups may also be substituted.

The 2β-position may also carry amino substituents, e.g. amino or substituted amino groups, for example mono- or di-alkylamine or saturated, unsaturated or aromatic heterocyclic amino groups, e.g. a morpholino group.

Particularly useful anaesthetic compounds in accordance with the invention are the 21-ethers of 3α,21-dihydroxy-5α-pregnane-11,20-dione.

The 21-ether substituent is preferably an alkoxy, cycloalkoxy, aralkoxy or aryloxy group which may carry substituents such as primary, secondary or tertiary amino groups, including heterocyclic groups, or carboxyl and esterified carboxyl groups, cyano groups and halogen atoms, e.g. chlorine atoms.

The amino substituent is conveniently a group of formula —NR$^1$R$^2$ and wherein R$^1$ and R$^2$, which may be the same or different, each represents a hydrogen atom or a lower (C$_1$–C$_4$) alkyl group or R$^1$ and R$^2$ together with the adjacent nitrogen atom represent a 5- or 6-membered heterocyclic group, e.g. a piperidino, piperazino or morpholino group which may, if desired, be substituted by at least one alkyl group; examples of such groups include an amino group, a methylamino group, a dimethylamino group, an ethylamino group, a diethylamino group or an N-methylpiperazino group.

A particularly preferred group of the above compounds are those wherein the 21-ether group is a lower alkoxy (C$_1$–C$_6$) group, which may be substituted, e.g. by a lower alkoxy (C$_1$–C$_6$) group; examples of such groups are methoxy, ethoxy, n-propoxy, isopropoxy and methoxyethoxy groups. Other compounds according to the invention are compounds wherein the 21-ether group is a phenoxy, cyclopentyloxy or benzyloxy group.

One group of preferred compounds in accordance with the invention are compounds carrying at least one primary, secondary or tertiary amino group or at least one carboxyl group, the invention including non-toxic salts of such compounds. By the term "non-toxic" as applied to the compounds of the invention we mean those derivatives which are physiologically acceptable in the dosage at which they are administered. As will be appreciated, amino and carboxy substituents of the type just referred to permit the formation of salts tending to improve the water-solubility of the steroid. Such salts include, in the case of amino-substituted compounds, hydrochlorides, hydrobromides, phosphates, sulphates, p-toluenesulphonates, methanesulphonates, citrates and tartrates. In the case of carboxy-substituted compounds, examples of salts include alkali metal, e.g. sodium or potassium salts and ammonium salts and other salts formed with physiologically compatible amines.

Examples of amino- or carboxy-substituted 21-ether groups include p-aminophenoxy, carboxyphenoxy, diethylaminoethoxy, morpholinoethoxy, carboxyethoxy and N-methyl-piperazinoethoxy groups.

Particularly preferred compounds according to the invention by virtue of their excellent anaesthetic properties are:

3α-hydroxy-21-n-propoxy-5α-pregnane-11,20-dione;
3α-hydroxy-21-methoxy-5α-pregnane-11,20-dione;
21-ethoxy-3α-hydroxy-5α-pregnane-11,20-dione;
3α-hydroxy-21-(2-methoxyethoxy)-5α-pregnane-11,20-dione;
21-(2-chloroethoxy)-3α-hydroxy-5α-pregnane-11,20-dione;
21-(3-chloropropoxy)-3α-hydroxy-5α-pregnane-11,20-dione;
21-cyclopentyloxy-3α-hydroxy-5α-pregnane-11,20-dione; and
3α-hydroxy-21-methoxy-16α-methyl-5α-pregnane-11,20-dione.

The above-defined 3α-oxygenated-pregnane-21-ether anaesthetics may be formulated as convenient, following generally known pharmaceutical practices, (including both human and veterinary medical practices), with the aid of one or more pharmaceutical carriers or excipients. For anaesthetic purposes, the steroids will be given by injection and thus one aspect of this invention comprises an anaesthetic composition for parenteral administration comprising a 3α-oxygenated-21-ether-pregnane anaesthetic as above-defined in a parenterally acceptable vehicle.

Many of the above-described 3α-oxygenated-21-ether-pregnane anaesthetics are poorly soluble in water. We have found however that they may be formulated for parenteral administration in an aqueous solution of a parenterally acceptable non-ionic surface active agent. These surface active agents may also be used even where the steroid is sufficiently water soluble as they may reduce the risk of thrombophlebitis.

The non-ionic surface active agents used for the purpose of this invention are generally those of the water-soluble type, conveniently having an HLB value of at least 9, preferably at least about 12, advantageously at least about 13. Preferably the HLB value of the surface active agent is not greater than about 15 although it may, for example, be as high as 18. The surface active agent must naturally be one which is physiologically compatible, i.e. of itself give rise to no physiologically unacceptable side effects in the dosages employed in the intended species to be treated (man or animal). Surface active agents for use in accordance with the invention are for example to be found among the following non-ionic surfactants and classes of surfactants: Polyoxyethylated derivatives of fatty (C12–C20) glyceride oils, e.g. castor oil, containing from 35 to 45 or even up to 60, oxyethylene groups, per mole of fatty oil. Polyoxyethylene ethers (containing from 10 to 30 polyoxyethylene groups) of long chain alcohols (containing for example from 12–18 carbon atoms).

Polyoxyethylene-polyoxypropylene ethers containing from 15 to 35 and from 15 to 30 oxyethylene and oxypropylene groups respectively. Polyoxyethylene ethers (containing from 6 to 12 oxyethylene groups) of alkyl phenols the alkyl groups of which preferably contain 6–10 carbon atoms.

Polyoxyethylated (containing from 15 to 30 oxyethylene groups) fatty acid (e.g. C12–18) esters of sugar alcohol anhydrides, e.g. sorbitan or mannitan. Long-chain (e.g. C10–16) alkanoyl mono- and dialkanolamides (the alkanol portions of which for example contain 1–5 carbon atoms) for example lauroyl mono- and di-ethanolamides. Polyethylene glycol esters (containing from 6 to 40 ethylene oxide units) of long chain fatty acids (containing for example 12–18 carbon atoms) e.g. polyethyleneglycol monooleate (containing for example 8 ethylene oxide units.)

Examples of non-ionic surface active agents, of the foregoing types, useful in accordance with the invention include:

Cremophor EL, a polyoxyethylated castor oil containing about 40 ethylene oxide units per triglyceride unit;

Tween 80, polyoxyethylene sorbitan monooleate containing about 20 ethylene oxide units;

Tween 60, polyoxyethylene sorbitan monostearate containing about 20 ethylene oxide units; and Tween 40, polyoxyethylene sorbitan monopalmitate containing about 20 ethylene oxide units.

The expression "solutions" is used herein to denote liquids which have the appearance of true solutions and are thus optically clear and capable of passage, for example, through a micro-porous filter, irrespective of whether such solutions are true solutions in the classical chemical sense and irrespective of whether they are stable or metastable. Thus it may be that the steroid is associated with micelles. The solutions of this invention, irrespective of their precise physical nature, behave as true solutions for the practical purpose of intravenous injection.

The proportion of surface active agent to be used in the compositions of this invention depends upon its nature and upon the concentration of steroid desired in the final composition.

In preferred compositions according to the invention the proportion of surfactant is preferably at least 5% by weight and advantageously above 10% by weight. A very convenient proportion of surfactant has been found to be 20% by weight but 30% and up to 50% may be used. The proportions of surfactant are expressed by weight in relation to the total volume of the composition.

As will be clear, the proportion of steroid which is dissolved in the aqueous solution according to the invention depends upon the nature and amount of surface active agent used. The composition will generally contain at least 1 mg/ml of steroid and solutions can be made containing for example up to 7 mg/ml of steroid or even 10 mg/ml.

In one method of preparing the solutions according to the invention the steroid is first dissolved in the selected surfactant, for example with heating, and the resulting solution dissolved in water. Alternatively the steroid may be dissolved in a volatile organic solvent advantageously having a boiling point of less than about 80°C which is miscible with the surface active agent such as a volatile lower aliphatic ketone e.g. acetone or methyl ethyl ketone or a volatile halogenated hydrocarbon, e.g. chloroform or methylene chloride. The surface active agent is then added to this solution, the organic solvent removed by evaporation, for example by passing a stream of an inert gas through the solution e.g. nitrogen and the resulting solution of steroid in surfactant is mixed with water.

The solutions may also be prepared by shaking the steroid with an aqueous solution of the surface active agent.

In all cases simple tests enable one to determine the relative proportions of surface active agent required.

The anaesthetic solutions according to the invention are generally administered by intravenous injection although as is known in the anaesthetic art in certain cases, e.g. with young children, intramuscular injection might be preferred.

As is usual in the case of anaesthetics, the quantity of steroid used to induce anaesthesia depends upon the weight of the individual to be anaesthetised. For intravenous administration in the average man a dose of from 0.5 to 30 mg/Kg will in general be found to be satisfactory to induce anaesthesia, the preferred dose being within the range of from 0.7 to 20 mg/Kg. The dose will naturally vary to some extent dependent upon the physical condition of the patient, and the degree and period of anaesthesia required, all as is well known in the art. It is thus possible by adjustment of the dose to achieve durations of anaesthesia varying from about 10 minutes to up to an hour or more. If it is desired to maintain prolonged anaesthesia, repeated doses of the solutions of this invention may be used, such repeated doses being generally either of the same order or lower than the original dose. Alternatively continuous administration may be undertaken at for example a rate of 0.09–14 mg/Kg/Min.

Where the anaesthetic solutions are administered intramuscularly, higher doses are generally necessary.

The new compounds according to the invention may be prepared in principle by the reaction of an appropriately substituted 21-hydroxy-pregnane compound or a reactive derivative thereof with an alcohol or phenol (or reactive derivative thereof) to form the desired ether group. It will be appreciated that the formation of the ether linkage at position 21 may be effected as a final step in the synthesis of the desired compound, or alternatively at some intermediate stage during the elaboration of the desired molecule, subsequent stages involving for example introduction of additional substitution, e.g. at the 2β-position.

The ether linkage at position 21 may be formed in conventional manner, general methods for the formation of ethers being described for example in the textbook "Chemistry of the Ether Linkage" by Saul patai (Interscience Publishers, London, New York and Sydney, 1967).

In one embodiment of the above method, the 21-hydroxy steroid or the said alcohol is reacted with a diazo derivative of the other reactant to form the desired ether.

Thus for example a 21-diazo-pregnan-20-one may be reacted with an appropriate alcohol, in conventional manner, if desired to the presence of a catalyst, e.g. cupric oxide or boron trifluoride. This reaction, which is particularly suitable for the production of aliphatic and araliphatic ethers is conveniently carried out in a solvent medium which may be an excess of the etherifying alcohol or a further co-solvent, for example an ether such as diethyl ether, tetrahydrofuran or dioxan, or a halogenated hydrocarbon, e.g. methylene chloride, chloroform etc, under anhydrous conditions.

Generally the reaction is effected at elevated temperature for example at the boiling point of the solvent used.

The diazo ketones required as starting materials are conveniently prepared in conventional manner from the corresponding $17\beta$-chlorocarbonyl steroids preferably in the presence of a tertiary organic base such as triethylamine) with a diazoalkane.

During the formation of the acid chlorides, the conversion to the subsequent diazo ketones and the subsequent reaction to form the ether, it may be desired to protect the $3\alpha$-hydroxy group.

Protection of $3\alpha$-hydroxy groups can be effected in conventional manner with the formation of a readily removable protecting group e.g. a nitrate, silyl, or acyl group. The protective group at position 3 can be removed in conventional manner, as desired, by, for example, hydrolysis or reduction as may be appropriate to the particular protective group, all as is well known in the art.

In a further embodiment of the above method of preparing the ethers in accordance with the invention the appropriate 21-hydroxy-pregnane compound may be reacted with a diazo compound, for example a diazoalkane, such as diazomethane in conventional manner. This reaction is carried out in generally similar manner to the above-described reaction of a steroid 21-diazo-20-ketone using a catalyst as may be necessary, for example boron trifluoride.

In yet a further embodiment a 21-halo-pregnane compound, e.g. a 21-bromo- or 21-iodo compound may be reacted with a metal derivative of the etherifying hydroxylic compound. Suitable metal derivatives are alkali metal, e.g. sodium or potassium derivatives, the reaction being particularly applicable to the formation of ethers from aromatic hydroxy compounds such as phenol and substituted phenols. Similarly, a 21-hydroxy pregnane can be reacted with a halide derivative of an alcohol (that is a derivative in which the hydroxyl group has been replaced by halogen) in the presence of silver oxide.

This reaction may be effected in a solvent medium, for example, in an aliphatic ketone, such as acetone or methyl ethyl ketone, e.g. at a temperature of 0° to 100°C.

It will be appreciated that where it is desired to form 21-ethers in accordance with the invention having a water-soluble group, it may be desirable first to form an ether having a group convertible to a group of the last-mentioned kind; for example in the preparation of compounds having at position 21 a grouping carrying a primary amino substituent, for example an aminophenyl ether, it is convenient first to form the corresponding nitro compound which can thereafter be readily reduced, in conventional manner, e.g. by hydrogenation or by chemical methods such as reduction with a metal/acid system.

The $3\alpha$-hydroxy pregnane 21-ethers according to the invention may also, for example, be prepared from the corresponding $3\beta$-hydrocarbonsulphonyloxy-pregnane 21-ethers by reaction with a salt of a carboxylic acid in a manner analogous to that described by Nagata et al. (Helv. Chim. Acta., 1959, 42, 1399) followed, if desired, by hydrolysis of the $3\alpha$-esters so formed to liberate the $3\alpha$-hydroxy group.

Compounds according to the invention having a $3\alpha$-hydroxy group and an $5\alpha$-hydrogen atom may be prepared from the corresponding 3-oxo pregnane-21-ethers by stereospecific reduction using chloroiridic acid. The iridium reduction is preferably carried out by first preforming an iridium catalyst reduction system from an iridium salt or acid (e.g. chloroiridic acid), an ester of phosphorous acid (e.g. trimethyl phosphite), water, and an organic reaction medium (e.g. an alcohol such as isopropanol). This reduction system is then preferably neutralised with an organic base (e.g. triethylamine), and reacted with the steroid.

A still further method of preparing the 21-ethers according to the invention is provided by the reaction of a $20\beta,21$-epoxide with an alcohol or phenol, preferably in the presence of an acid catalyst conveniently a mineral acid such as sulphuric acid or a Lewis acid such as boron trifluoride (as the etherate), to form a $20\beta$-ol-21-ether; this may then be oxidised by any reagent serving to oxidise a secondary alcohol to a ketone, for example a chromic oxidising agent, which may, for example a chromic acidic, e.g. chromic acid in acetone, or basic, e.g. using pyridine-chromium trioxide complex in a solvent such as pyridine, benzene or methylene chloride.

During the above oxidation, the $3\alpha$-hydroxy group will normally be oxidised to a 3-oxo group but can be regenerated by stereospecific reduction; for example on the $5\alpha$-series with chloroiridic acid and in the $5\beta$-series with a borohydride. Alternatively, the $3\alpha$-hydroxy group may be protected, for example by conversion into a selectively cleavable ester or ether group, e.g. a nitro-oxy group or an ester group of a type desirable in the final product, e.g. an acetyl group. The nitro-oxy group can readily be removed finally by acid hydrolysis or more selectively, by reduction, e.g. by hydrogenation using a palladium catalyst or zinc/acetic acid reduction. This reduction may dehalogenate any haloalkyl substituents which are present and if such substituents are required in the final product, alternative methods will be preferable.

The $20\beta,21$-epoxides may conveniently be prepared from corresponding 20-ketones having at the 21-position a readily eliminatable substituent, (such as a chlorine, bromine or iodine atom or a hydrocarbon-sulphonyloxy group such as a p-toluenesulphonyloxy or methanesulphonyloxy group) by reduction of the 20-keto group (e.g. using a borohydride reducing agent, for example calcium, sodium or potassium borohydride), the $20\beta$-ol so formed then being converted into the $20\beta,21$-epoxide under basic conditions. Where an 11-oxo group is present, reduction under said conditions will normally not attack this grouping but if reduction to the $11\beta$-ol does take place under more vigorous conditions, reoxidation can be effected simultaneously with oxidation of the $20\beta$-hydroxy group. The starting compound can thus carry an 11-hydroxy group capable of such oxidation in the final stage.

The basic conditions for epoxide formation may be achieved by adding a strong base, e.g. an alkali metal hydroxide, for example aqueous sodium hydroxide, conveniently in an organic solvent such as tetrahydrofuran or dioxan. The reaction is often nearly quantitative. It is not necessary to isolate the initial 20-ol reduction products but where it is desired to avoid reducing an 11-keto group, it is best to destroy any residual borohydride, e.g. by addition of an acid such as acetic acid, before adding the base. In some cases, the quantity of borohydride reagent used creates sufficiently basic conditions for epoxide formation without added base.

Some $20\alpha$-ol may be formed in the reduction and lead to a $20\alpha,21$-epoxide, but on reaction with the alcohol or phenol it will give products capable of subsequent oxidation to 20-one. Consequently mixtures of $20\alpha$-, and $20\beta$-ol do not need to be separated before base treatment. It should be noted that the 3-position in the 20-keto starting material may carry a protected $3\alpha$-hydroxyl group (which remains throughout the reaction), a $3\alpha$- or, indeed, a $3\beta$-hydroxy group (which may be oxidized to 3-ketone simultaneously with the 20-ol) or a 3-oxo group (which will be reduced to $3\beta$-hydroxyl by the reducing agent but re-oxidized simultaneously with the 20-ol). As indicated above, 3-keto as can subsequently be stereospecifically reduced to $3\alpha$-ols.

Protection of the $3\alpha$-hydroxy group can conveniently be effected by nitration e.g. using fuming nitric acid in acetic anhydride and we have found this reaction to proceed readily and in high yield on, for example, 21-bromo-20-ketones.

It should be noted that the foregoing process in which the 20-keto group is reduced at an early stage minimizes the tendency towards 17-isomerisation caused by enolisation at the 20-position.

The 21-ether substituent may, as indicated above, advantageously carry a basic substituent. This can conveniently be introduced by reacting a corresponding 21-ether carrying a readily eliminatable substituent in the ether group (e.g. a halogen atom such as chlorine or bromine) with ammonia or a suitable amine. The 21-ether starting material can be made particularly conveniently by reacting the 20,21-epoxides described above with the appropriate alcohol or phenol carrying the eliminatable substituent. We have found that boron trifluoride etherate is an especially effective catalyst in this case, particularly in relation to the reactions with ethylene chlorohydrin and 3-chloropropanol.

It is found that protection of the $3\alpha$-hydroxy group as the nitrate can readily be adopted, as the subsequent removal by reduction with zinc and acetic acid does not attack the amino group. Alternatively, as indicated above, the $3\alpha$-hydroxy group can be allowed to oxidise to 3-ketone but it is then found preferable to effect stereospecific reduction to the desired $3\alpha$-hydroxy steroid before the final reaction with amounts or an amine.

For the introduction of a 21-ether group carrying a carboxyl or esterified carboxyl group, a corresponding compound in which the 21-ether group carries a cyano group may be solvolysed. The reaction is preferably effected in the presence of an alcohol, e.g. using ethanolic hydrogen chloride, to give an esterified carboxyl group which may subsequently be converted to a carboxyl group if desired, e.g. by basic hydrolysis. The cyano-ether grouping may conveniently be introduced by reacting a corresponding 20,21-epoxide with a cyano-alcohol, advantageously in the presence of boron trifluoride etherate as a catalyst. As before, the $3\alpha$-hydroxy group may be protected or left unprotected or a $3\beta$-ol or 3-ketone may be used as starting material.

Salts of the new acidic and basic 21-ethers prepared by known methods. Compounds of formula I containing a basic substituent may be converted into acid addition salts thereof for example by reaction of the free base with the appropriate organic or inorganic acid conveniently in solution in an organic solvent. The preparation of salts of 21-ethers which contain a carboxy substituent may be effected, for example by reaction of the free acid, conveniently in a solvent, with an appropriate base.

Substitution in the steroid molecule can be carried out in conventional manner, either prior to or after formation of the ether group at position 21. Substitution at the 2-position can be effected for example by way of the corresponding $2\alpha,3\alpha$-epoxy compound. The epoxy compound itself may be prepared by first dehydrating a $3\alpha$-hydroxy compound to give the corresponding $\Delta^2$ compound (e.g. by first tosylating the hydroxy group and then detosylating the product), and then treating the $\Delta^2$ compound with a peracid to form the $2\alpha,3\alpha$ epoxide ring. A $2\beta$-substituent, Z, may then be introduced and the $3\alpha$-hydroxy group regenerated by reacting the $2\alpha,3\alpha$-epoxy compound with a compound of the formula ZH or a compound furnishing an anion $Z^-$ and a cation, followed, where a metal derivative of the $3\alpha$-hydroxy group is first formed, by treatment with a source of protons.

The $3\alpha$-acyloxy-pregnane anaesthetics may be prepared from the corresponding $3\alpha$-hydroxy-pregnanes by acylation for example, in known manner. Acylation under basic conditions is generally preferred in order to avoid undesired side reactions.

The acylating agent may for example be the anhydride or a halide (preferably the chloride) of the corresponding carboxylic acid. In general, the acylation is effected in the presence of a tertiary organic base such as pyridine, 4-methylpyridine or N-methylmorpholine.

The acylation is generally effected in a solvent preferably an aprotic solvent which may, for example, be an excess of the acylating agent and/or an excess of a tertiary organic base, if desired in the presence of a co-solvent, for example tetrahydrofuran.

Substitution at position 16 can also be carried out in conventional manner, various methods for this purpose being well known in the art.

Compounds in which the 16-position carries a $16\alpha$-alkyl group may be prepared from 16,17-dehydro-20-oxo-steroids by reaction with a lithium dialkyl cuprate; a 16,17-dehydro-$2\alpha,3\alpha$-epoxide reacts with this reagent to form a $2\beta,16\alpha$-dialkyl derivative, the two reactions being effected simultaneously.

The 21-bromo steroids used as intermediates in the present processes may conveniently be prepared by halogenation of a corresponding 21-unsubstituted 20-keto pregnane, for example with molecular bromine, in an alcohol solvent advantageously in the presence of catalyst such as acetylchloride or hydrogen bromide. 21-Hydroxy steroids may be obtained by lead tetraacylate oxidation of such 21-unsubstituted 20-keto pregnanes whereby a 21-acyloxy group is introduced followed by basic hydrolysis to yield a 21-hydroxy group. In these reactions the $3\alpha$-hydroxy group is preferably protected; the nitrooxy group has proved particularly useful and resists the basic hydrolytic conditions for removal of the 21-acyloxy group. 21-Iodo steroids can be obtained from 21-chloro steroids by halogen exchange, e.g. by reaction with sodium iodide.

For the better understanding of the invention the following Preparations and Examples are given by way of illustration only.

All temperatures are in degrees Celsius. The term petrol as used herein refers to petroleum ether (b.p. 60°–80°).

All rotations were carried out in chloroform at approximately 1% w/v concentration unless otherwise stated:

Stock' chloroiridic acid solution was prepared by refluxing a mixture of chloroiridic acid (0.09 g.), isopropyl alcohol containing 10% water (200 ml.) and trimethylphosphite (16 ml.) for 16 hours. The solution was neutralised with triethylamine immediately prior to use.

Jones' reagent refers to a solution of chromium trioxide (267 g.) in a mixture of concentrated sulphuric acid (230 ml.) and water (400 ml.) made up to 1 liter with water (8N w.r.t. oxygen).

Preparative thin layer chromatography (preparative t.l.c.) was carried out on silica gel.

PREPARATION 1

21-Hydroxy-3α-nitro-oxy-5α-pregnane-11,20-dione

3α-Hydroxy-21-acetoxy-5α-pregnane-11,20-dione (5 g.) in chloroform (25 ml.) was added to a stirred solution of fuming nitric acid (13 ml.) in acetic anhydride (50 ml.) at −5°. The reaction mixture was stirred at −5° for an hour, poured into stirred aqueous sodium hydroxide (1 l.) and extracted with chloroform. The extract was washed with aqueous sodium hydrogen carbonate and with water, dried ($Na_2SO_4$) and evaporated to a white froth. This was dissolved in methanol (500 ml.), the solution flushed with nitrogen and stirred with 10% aqueous potassium hydrogen carbonate (17.5 ml.) for four hours. Glacial acetic acid (3 ml.) was added, the solution evaporated to small bulk, poured into water (1 l.) and extracted with chloroform, washed with water, dried ($Na_2SO_4$) and evaporated to a white froth. Crystallisation from acetone/ether gave title compound (4.31 g.) as colourless irregular prisms, m.p. 174°–181°.

PREPARATION 2

21-Methoxy-3α-nitro-oxy-5α-pregnane-11,20-dione

A solution of 21-hydroxy-3α-nitro-oxy-5α-pregnane-11,20-dione (700 mg.) in dry methylene chloride (30 ml.) and dry ether (30 ml.) was treated with an excess of a solution of diazomethane in ether, in the presence of boron trifluoride etherate (8 drops). When the solution remained yellow on addition of further diazomethane, the solution was evaporated to a residue. Purification by preparative t.l.c. gave title compound (170 mg.) as a white foam $[\alpha]_D + 92°$.

PREPARATION 3

3α-Nitro-oxy-11-oxo-5α-androstane-17β-carboxylic acid

A solution of 3α-nitro-oxy-21-hydroxy-5α-pregnane-11,20-dione (3 g.) in methanol (30 ml.) and tetrahydrofuran (25 ml.) was stirred with sodium metaperiodate (1.8 g.) in water (10 ml.) for five days. The solution was diluted with chloroform, washed with 2N-hydrochloric acid and with water, dried ($Na_2SO_4$) and evaporated to a residue. Crystallisation from benzene and chloroform gave title compound (1.58 g.) as colourless rods; m.p. 214°–216° (dec.); $[\alpha]_D + 72°$.

PREPARATION 4

21-Diazo-3α-nitro-oxy-5α-pregnane-11,20-dione

A solution of 3α-nitro-oxy-11-oxo-5α-androstane-17β-carboxylic acid (3.5 g.) in dry benzene (100 ml.) and dry tetrahydrofuran (50 ml.) was refluxed with oxalyl chloride (12 ml.) for 1½ hours. The solution was evaporated to give 17β-chlorocarbonyl-3α-nitro-oxy-5α-androstan-11-one as a foam which was dried in vacuo. A solution of this foam in benzene (100 ml.) was added to an excess of a solution of diazomethane in ether at −10°. The mixture was allowed to warm to room temperature. After one hour any excess of diazomethane was removed by bubbling nitrogen through the mixture. The solution was evaporated to a yellow foam. Purification by preparative t.l.c. followed by crystallisation from acetone, ether and petrol gave title compound (82 mg.) as yellow plates; m.p. 155°–160° (dec.) $[\alpha]_D + 145°$.

PREPARATION 5

21-Bromo-3α-hydroxy-5α-pregnane-11,20-dione

3α-Hydroxy-5α-pregnane-11,20-dione (1 g.) in stirred methanol (7 ml.) at 30° was treated with acetyl chloride (1 drop). After two minutes bromine (0.19 ml.) in methanol (4.5 ml.) was added dropwise. The solution being allowed to decolourise between the addition of each drop. The resulting clear solution was poured into chloroform (100 ml.), washed with water (3 × 50 ml.) dried ($Na_2SO_4$) and evaporated to a white froth (1.40 g.). Preparative t.l.c. afforded title compound (715 mg.) which crystallised from chloroform/ether as clusters of colourless needles, m.p. 160°–163°; $[\alpha]_D + 109°$ (c 0.82).

PREPARATION 6

3α-Hydroxy-16α-methyl-5α-pregnane-11,20-dione

To a stirred slurry of cuprous iodide (950 mg.) in dry ether (75 ml.) under dry nitrogen at 0° was added a solution of methyl-lithium in ether (c 1.6M; 6 ml.) until the initially formed yellow precipitate just redissolved to give a clear solution. To the stirred solution at 0° was added a solution of 3α-hydroxy-5α-pregn-16-ene-11,20-dione (600 mg.) in dry tetrahydrofuran (50 ml.). During the addition a bright yellow precipitate formed. The mixture was stirred at 0° for 30 minutes, and then poured into cold, saturated ammonium chloride solution (200 ml.). More ether (200 ml.) was added, and the organic layer was separated, washed with saturated ammonium chloride solution (200 ml.) and with water (200 ml.) dried over sodium sulphate and purified by preparative t.l.c. in ethyl acetate to give a product which was further purified by preparative t.l.c. in ethyl acetate/chloroform, 1/1 to give a white solid (380 mg.) which was recrystallised from ether/petrol to give title compound (248 mg.) as colourless plates, m.p. 138°–140°, $[\alpha]_D + 99°$, (c 0.95).

PREPARATION 7

20β,21-Epoxy-3α-hydroxy-5α-pregnan-11-one

21-Bromo-3α-hydroxy-5α-pregnane-11,20-dione (404 mg.) in methanol (25 ml.) was stirred at room temperature with sodium borohydride (39 mg.) in water (5 ml.). After 30 minutes acetic acid (0.1 ml.) was added, the solvents were evaporated and the residue was partitioned between water and chloroform. The organic layer was dried (MgSO$_4$) and evaporated to a froth (443 mg.). This was taken up in tetrahydrofuran (25 ml.) and stirred under nitrogen with 2N aqueous sodium hydroxide (2 ml.). After five hours the solution was partitioned between ether and water. The organic phase was washed with water, dried (Na$_2$SO$_4$) and evaporated to a crystalline solid (300 mg.). Recrystallisation from chloroform/ether gave title compound (202 mg.) as colourless rods; m.p. 235°–242°; [α]$_D$ + 18.0°, (c 1.06).

PREPARATION 8

21-bromo-3α-nitro-oxy-5α-pregnane-11,20-dione

A solution of 21-bromo-3α-hydroxy-5α-pregnane-11,20-dione (311 mg.) in chloroform (3 ml.) was added slowly with stirring to fuming nitric acid (0.8 ml.) and acetic anhydride (3 ml.), the temperature being kept between −5° and −10° for one hour. The solution was then poured into stirred aqueous sodium hydroxide (15 ml. 2N NaOH in 50 ml. water) to yield a resultant solution of pH 4, which was extracted with chloroform washed with saturated sodium bicarbonate solution, water, dried (Na$_2$SO$_4$) and evaporated to a white solid (324 mg.). Recrystallisation of this solid from acetone and petrol yielded title compound (243 mg.) as lemon irregular prisms; m.p. 121°–128°; [α]$_D$ + 108° (c 0.94).

PREPARATION 9

21-bromo-20β-hydroxy-3α-nitro-oxy-5α-pregnan-11-one

A solution of 21-bromo-3α-nitrooxy-5α-pregnane-11,20-dione (2.87 g.) in methanol (60 ml.) and dry tetrahydrofuran (20 ml.) was stirred with sodium borohydride (240 mg.) in water (10 ml.). After 15 minutes, glacial acetic acid (0.3 ml.) was added and a fraction (9 ml.) of the reaction mixture was isolated. This fraction was evaporated to dryness and a solution of the residue in ether (50 ml.) was washed with water, dried (Na$_2$SO$_4$) and evaporated to a white foam (261 mg.). Crystallisation of this foam from chloroform and ether yielded title compound (110 mg.) as white rods; m.p. 170°–174°.

PREPARATION 10

20β,21-epoxy-3α-nitro-oxy-5α-pregnan-11-one

A solution of 21-bromo-3α-nitro-oxy-5α-pregnane-11,20-dione (1.01 g.) in methanol (20 ml.) and dry tetrahydrofuran (20 ml.) was stirred with sodium borohydride (84 mg.) in water (4 ml.) at room temperature. After one hour, glacial acetic acid (0.1 ml.) was added and the resultant solution was stirred, under nitrogen, with 2N sodium hydroxide (4 ml.). After ½ hour, the solvent was evaporated and the residue was stirred with water (200 ml.) for thirty minutes, filtered, washed with water and dried (756 mg.). Recrystallisation of the crude product from ether yielded title compound (275 mg.) as white rods; m.p. 147°–159°; [α]$_D$ + 23.5° (c 1.02).

PREPARATION 11

20β-hydroxy-21-methoxy-3α-nitro-oxy-5α-pregnan-11-one

A solution of 20β,21-epoxy-3α-nitro-oxy-5α-pregnan-11-one (513 mg.) in dry methanol (25 ml.) was treated with concentrated sulphuric acid (2 drops) at room temperature. After one hour, the solution was neutralised with saturated sodium bicarbonate solution and the solvent evaporated. A solution of the residue in chloroform (150 ml.) was washed with water, dried (Na$_2$SO$_4$) and evaporated to a white foam (554 mg.), 209 mg. of which was purified by preparative t.l.c. (ethyl acetate 1:2 benzene) to yield a white foam (162 mg.). Crystallisation of this foam from ethyl acetate and petrol yielded title compound (90 mg.) as white rods; m.p. 150°–155°; [α]$_D$ + 38° (c 1.29).

PREPARATION 12

21-Methoxy-3α-nitro-oxy-5α-pregnane-11,20-dione

A solution of 20β-hydroxy-21-methoxy-3α-nitro-oxy-5α-pregnan-11-one (310 mg.) in acetone (20 ml.) was stirred at 0° and treated with Jones' reagent until oxidation was complete. The mixture was partitioned between ether and water and the ether extract was washed with water, dried (Na$_2$SO$_4$) and evaporated to a white solid (222 mg.). This solid was purified by preparative t.l.c. (ethyl acetate 1:2 benzene) and the major component obtained was crystallised from ethyl acetate and petrol to yield title compound (63 mg.) as white needles; m.p. 156°–162°; [α]$_D$ + 97°, (c 0.97°).

PREPARATION 13

3α-Hydroxy-21-bromo-16α-methyl-5α-pregnane-11,20-dione

3α-Hydroxy-16α-methyl-5α-pregnane-11,20-dione (5 g.) was dissolved in dry methanol (350 ml.) and treated at 0° with a solution of bromine (1 ml.) in dry methanol (24 ml.) at such a rate that the yellow colour disappeared before further addition. After completion of the addition the mixture was poured into water. The precipitated product was dried and dissolved in chloroform (20 ml.) and put onto a column of silica gel MFC (700 g.). Elution with benzene:ethyl acetate (2½:1) gave the title compound (3.6 g.) as a foam, [α]$_D$ + 112.4°.

EXAMPLE 1

3α-Hydroxy-21-methoxy-5α-pregnane-11,20-dione

A solution of 21-diazo-3α-nitro-oxy-5α-pregnane-11,20dione (3 g.) in dry methylene chloride (40 ml.) and dry methanol (100 ml.) was refluxed with 14% boron trifluoride methanol complex (10 ml.) for 25 minutes. The mixture was evaporated to small volume, diluted with ether, washed with water, saturated sodium bicarbonate solution and again with water, dried (Na$_2$SO$_4$) and evaporated to give 21-methoxy-3α-nitro-oxy-5α-pregnane-11,20-dione as a solid residue.

A solution of this residue in glacial acetic acid (90 ml.) was stirred with zinc powder (10.6 g.) for 1½ hours. The mixture was filtered and the zinc washed with chloroform. The combined filtrates were washed with water, saturated sodium bicarbonate and again with water, dried (Na$_2$SO$_4$) and evaporated to a foam. Purification by preparative t.l.c. followed by crystallisation from ether gave title compound (530 mg.) as colourless irregular prisms, m.p. 144°–146° $[\alpha]_D + 98°$.

EXAMPLE 2

21-Ethoxy-3α-hydroxy-5α-pregnane-11,20-dione

A solution of 21-diazo-3α-nitro-oxy-5α-pregnane-11,20-dione (2 g.) in dry ethanol (150 ml.) was refluxed with boron trifluoride etherate (5 ml.) for 20 minutes. The solution was evaporated to small volume, diluted with ether, washed with water, saturated sodium bicarbonate solution and again with water, dried (Na$_2$SO$_4$) and evaporated to give 21-ethoxy-3α-nitro-oxy-5α-pregnane-11,20-dione as a foam. A solution of the foam in glacial acetic acid (50 ml.) was stirred with zinc powder (5.4 g.) for 1¼ hours. The mixture was filtered and the zinc washed with chloroform. The combined filtrates were washed with water, dried (Na$_2$SO$_4$) and evaporated to a foam. Purification by preparative t.l.c. followed by crystallisation from ethyl acetate and petrol gave title compound (200 mg.) as colourless plates, m.p. 129°–131° $[\alpha]_D + 98.5°$.

EXAMPLE 3

3α-Hydroxy-21-propoxy-5α-pregnane-11,20-dione

A solution of 21-diazo-3α-nitro-oxy-5α-pregnane-11,20-dione (900 mg.) in dry propanol (50 ml.) was treated with boron trifluoride etherate (1 ml.) and refluxed for 10 minutes. The mixture was evaporated to small volume, diluted with ether, washed with water, saturated sodium bicarbonate solution and again with water, dried (Na$_2$SO$_4$) and evaporated to a foam. Purification by preparative t.l.c. gave 3α-nitro-oxy-21-propoxy-5α-pregnane-11,20-dione as a foam. A solution of this foam in glacial acetic acid (20 ml.) was stirred with zinc powder (2.3 g.) for 1½ hours. The mixture was filtered, and the zinc washed with chloroform. The combined filtrates were washed with water, dried (Na$_2$SO$_4$) and evaporated to give title compound (480 mg.) as a white foam, $[\alpha]_D + 91.5°$.

EXAMPLE 4

3α-Hydroxy-21-isopropoxy-5α-pregnane-11,20-dione

A solution of 21-diazo-3α-nitro-oxy-5α-pregnane-11,20-dione (860 mg.) in dry isopropanol (60 ml.) was treated with boron trifluoride etherate (1 ml.) and refluxed for 20 minutes. The mixture was evaporated to small volume, diluted with ether, washed with water, saturated sodium bicarbonate solution and again with water, dried (Na$_2$SO$_4$) and evaporated to a residue. Crystallisation from ethyl acetate and petrol gave 3α-nitro-oxy-21-isopropoxy-5α-pregnane-11,20-dione (456 mg.) as off-white rods, m.p. 135°–139°, $[\alpha]_D + 92°$.

A solution of the nitrate (350 mg.) in glacial acetic acid (10 ml.) was stirred with zinc powder (1.2 g.) for 1¼ hours. The mixture was filtered and the zinc washed with chloroform. The combined filtrates were washed with water, saturated sodium bicarbonate solution and again with water, dried (Na$_2$SO$_4$) and evaporated to a residue. Purification by preparative t.l.c. followed by crystallisation from ethyl acetate and petrol gave title compound (189 mg.) as colourless rods, m.p. 121°–125°, $[\alpha]_D + 75.4°$.

EXAMPLE 5

3α-Hydroxy-21-(2'-methoxyethoxy)-5α-pregnane-11,20-dione

A solution of 21-diazo-3α-nitro-oxy-5α-pregnane-11,20-dione (500 mg.) in dry 2-methoxyethanol (10 ml.) was treated with boron trifluoride etherate (1 ml.) at 65°. After 10 minutes the solution was diluted with ether, washed with water, saturated sodium bicarbonate solution and again with water, dried (Na$_2$SO$_4$) and evaporated to give 21-(2'-methoxyethoxy)-3α-nitro-oxy-5α-pregnane-11,20-dione (460 mg.) as a foam. A solution of this foam in glacial acetic acid (10 ml.) was stirred with zinc powder (1 g.) for 1½ hours. The mixture was filtered and the zinc washed with chloroform. The combined filtrates were washed with water, saturated sodium bicarbonate solution and again with water, dried (Na$_2$SO$_4$) and evaporated to a residue. Purification by preparative t.l.c. followed by crystallisation from ether gave title compound (133 mg.) m.p. 115°–121° $[\alpha]_D + 76.7°$.

EXAMPLE 6

21-p-Aminophenoxy-3α-hydroxy-5α-pregnane-11,20-dione

A solution of p-nitrophenol (3.12 g.) in ethanol (10 ml.) and water (10 ml.) was treated with 0.2N-sodium hydroxide solution (105 ml.) and then evaporated to a residue that was dried in vacuo. A solution of this residue in acetone (200 ml.) was refluxed with a solution of 21-bromo-3α-hydroxy-5α-pregnane-11,20-dione (1.8 g.) in acetone (150 ml.) for 30 minutes. The mixture was evaporated to small volume, diluted with chloroform, washed with water, 2N-sodium carbonate solution and again with water, dried (Na$_2$SO$_4$) and evaporated to a residue. This was triturated with petrol and then crystallised from ethyl acetate and petrol to give 3α-hydroxy-21-p-nitro-phenoxy-5α-pregnane-11,20-dione (1.49 g.), m.p. 186°–187°, $[\alpha]_D + 58.5°$.

A solution of this (1 g.) in ethyl acetate (100 ml.) was shaken under hydrogen over 5% palladium-on-charcoal (100 mg.). After four hours the mixture was filtered and evaporated to a foam. Purification by preparative t.l.c. followed by crystallisation from ethyl acetate and petrol gave title compound (212 mg.) as off-white plates, m.p. 179°–180°, $[\alpha]_D + 42.5°$.

EXAMPLE 7

3α-Hydroxy-21-methoxy-16α-methyl-5α-pregnane-11,20-dione

The bromo-compound from Preparation 13 (3 g.) in methanol (70 ml.) and dry tetrahydrofuran (15 ml.) was stirred with sodium borohydride (300 mg.) and water (10 ml.) for 30 minutes. Glacial acetic acid (0.3 ml.) was then added and the mixture was stirred with 2N sodium hydroxide (18 ml.), for 1 hour. The mixture was poured into water, stirred and the precipitate was collected by filtration and dried at the pump to give 20β,21-epoxy-3α-hydroxy-16α-methyl-5α-pregnen-11-one (2.7 g.), which was treated with dry methanol (125 ml.) and boron trifluoride diethyl etherate (2 ml.), with stirring for 4 hours. The solution was neutralised with saturated aqueous sodium bicarbonate and evaporated. The residue was dissolved in chloroform (250 ml.), washed with water (3 × 200 ml.), dried (Na$_2$SO$_4$) and evaporated to give 3α,20β-dihydroxy- 21-methoxy-16α-methyl-5α-pregnan-11-one (2.4 g.). This, dissolved in acetone (175 c.c.), was treated with a slight excess of Jones' reagent until the oxidation was complete. The reaction mixture was partitioned between water and ether, the ether layer was washed with water (3 × 300 c.c.), dried ($Na_2SO_4$) and evaporated. The total crude product was refluxed for 18 hours in 'stock chloroiridic catalyst solution' (75 c.c.). The reaction mixture was partitioned between water and ether, the ether layer was washed with water (3 × 300 c.c.), dried ($Na_2SO_4$) and evaporated. The product was purified by preparative t.l.c. (ethyl acetate: chloroform, 1:1) to give 3α-hydroxy-21-methoxy-16α-methyl-5α-pregnane-11,20-dione (0.95 g.), $[\alpha]_D + 84.9°$.

EXAMPLE 8

3α-Hydroxy-21-methoxy-5α-pregnan-20-one

A stirred solution of 3α-hydroxy-5α-pregnan-20-one (5 g., 15.7 mmole) in AR methanol (350 c.c.) was treated at 0° with a solution of bromine (1 c.c.) in methanol (23 c.c.) at such a rate that the yellow colour disappeared before further addition. The resultant suspension was poured into water and stirred for 30 minutes, and the precipitate was collected by filtration and dried in vacuo. The product was purified by column chromatography on silica gel MFC, (700 g.). Elution with benzene:ethyl acetate, 1:1) gave 21-bromo-3α-hydroxy-5α-pregnan-20-one (5.2 g.) $[\alpha]_D + 105.5°$.

The total product (5.2 g.) in methanol (200 c.c.) and dry tetrahydrofuran (50 c.c.) was stirred with sodium borohydride (440 mg.) and water (20 c.c.). After 1 hour, glacial acetic acid (0.4 c.c.) was added followed by 2N sodium hydroxide (25 c.c.) and stirring was continued for a further 2 hours. The solution was then poured into water (1 l.) and stirred for 30 minutes, the precipitated 20β,21-epoxy-3α-hydroxy-5α-pregnane (4.9 g.) was collected by filtration and dried in vacuo (4.9 g.). It was treated with A.R. methanol (225 c.c.) in boron trifluoride diethyl etherate (2 c.c.), with stirring for 15 hours. The solution was then neutralised with saturated sodium bicarbonate solution and evaporated. The residue was dissolved in chloroform (500 c.c.), washed with water (3 × 300 c.c.), dried ($Na_2SO_4$) and evaporated to give 3α,20β-dihydroxy-21-methoxy-5α-pregnane (3.7 g.). This was dissolved in acetone (250 c.c.) was treated with a slight excess of Jones' reagent, until oxidation was complete. The reaction mixture was partitioned between water and ether and the ether layer was washed with water (3 × 300 c.c.), dried ($Na_2SO_4$) and evaporated. The product was recrystallised from acetone/petroleum ether to give 21-methoxy-5α-pregnane-3,20-dione as white needles, (1.85 g.) m.p. 156°, $[\alpha]_D + 141°$, (c 0.16).

The total crude product (1.85 g.) dissolved in 'stock' chloroiridic solution (90 c.c.) and the resulting solution was refluxed for 16 hours. The solution was allowed to cool and it was partitioned between water and ether. The ether layer was washed with water (3 × 300 c.c.), dried ($Na_2SO_4$) and evaporated. The crystalline residue was dried in vacuo and recrystallised from acetone/petroleum ether to give 3α-hydroxy-21-methoxy-5α-pregnan-20-one (0.84 g.), m.p. 163°–164° $[\alpha]_D + 85.4°$.

EXAMPLE 9

3α-Acetoxy-21-methoxy-5α-pregnane-11,20-dione.

A solution of 3α-hydroxy-21-methoxy-5α-pregnane-11,20-dione (0.2 g.) in pyridine (1.0 ml.) was treated with acetic anhydride (0.2 ml.) at room temperature for 16 hours. The mixture was then partitioned between ether and 2N-hydrochloric acid and the organic layer was washed with water, dried ($Na_2SO_4$) and evaporated. The residue was recrystallised from acetone/petroleum ether to give 3α-acetoxy-21-methoxy-5α-pregnane-11,20-dione (0.17 g.) as white needles; m.p. 93°; $[\alpha]_D + 107°$, (c 0.7).

EXAMPLE 10

3α-Hydroxy-2β, 21-dimethoxy-5α-pregnane-11,20-dione

3α-Hydroxy-21-methoxy-5α-pregnane-11,20-dione (1.5 g.) in dry pyridine (7.5 ml.) was treated with toluene p-sulphonyl chloride (1.5 g.) at room temperature overnight. The reaction mixture was then partitioned between 2N-hydrochloric acid and chloroform, washed with water, dried ($Na_2SO_4$) and evaporated to give 21-methoxy-3α-(p-toluene sulphonyloxy)-5α-pregnane-11,20-dione (1.55 g.) as a foam.

The total crude product in benzene was left in contact with alumina (grade H, 150 g.) for 24 hours and elution with benzene gave 21-methoxy-5α-pregn-2-ene-11,20-dione (0.7 g.) as an oil.

The total product was dissolved in chloroform (25 ml.) and m-chloroperbenzoic acid (0.51 g.) was added, the solution was stirred at room temperature overnight, diluted with chloroform, washed with dilute sodium bicarbonate, dried ($Na_2SO_4$) and evaporated to give 2α,3α-epoxy-21-methoxy-5α-pregnane-11,20-dione (0.7 g.) as an oil.

This was stirred in dry methanol (40 ml.) and treated with concentrated sulphuric acid (0.1 ml.) for 30 minutes. The product was partitioned between water and chloroform.

The solvent was removed from the chloroform extract and the residue was subjected to preparative t.l.c. in ethyl acetate-petroleum ether to give title compound (0.1 g.) as white needles, m.p. 168°–170°; $[\alpha]_D + 105°$, (c 0.9).

EXAMPLE 11

21-(2-Chloroethoxy)-3α-hydroxy-5α-pregnan-11,20-dione-3-nitrate

A solution of 20β,21-epoxy-3α-hydroxy-5α-pregnan-11-one 3-nitrate (1.0 g.) in ethylene chlorohydrin (25 ml.) was treated with boron trifluoride diethyl etherate (3 drops) at room temperature for 1½ hours. The solution was then partitioned between water and ether and the organic layer was washed with water, dried ($Na_2SO_4$) and evaporated.

The residue, crude 21-(2'-chloroethoxy)-3α, 20β-dihydroxy-5α-pregnan-11-one 3-nitrate (1.0 g.), was dissolved in acetone (75 ml.) and treated with Jones' reagent (1.5 ml.) at 0° for 5 minutes. The mixture was then partitioned between water and ether and the organic layer was washed with water, dried ($Na_2SO_4$) and evaporated. A portion of the residue (260 mg.) was subjected to preparative t.l.c. petrol/EtOAc 2:1) to give title compound (0.2 g.) as a white foam, $[\alpha]_D + 80°$ (c 1.2).

EXAMPLE 12

3α-Hydroxy-21-(2'-morpholinoethoxy)-5α-pregnane-11,20-dione

A solution of 21-(2'-chloroethoxy)-3α-hydroxy-5α-pregnane-11,20-dione 3-nitrate (0.560 g.) in morpholine (8 ml.) was heated on a steam bath for 1 hour, cooled and partitioned between water and ether. The organic layer was washed with water, dried ($Na_2SO_4$) and evaporated. The residue was subjected to preparative t.l.c. ($EtOAc/CHCl_3/(CH_3)_2CO$, 1:1:1) to give crude 3α-hydroxy-21-(2'-morpholinoethoxy)-5α-pregnane-11,20-dione 3-nitrate (0.4 g.).

A stirred solution of the nitrate (0.4 g.) in acetic acid (10 ml.) was treated with powdered zinc (1.0 g.) at room temperature for 30 minutes; poured into water, neutralised with 40% aqueous sodium hydroxide and extracted with ether. The extract was washed with water, dried ($Na_2SO_4$) and evaporated. The residue was subjected to preparative t.l.c. $EtOAc/CHCl_3/(CH_3)_2CO$ 1:1:1, and recrystallised from acetone to give title compound (0.2 g.,) as slightly pink prisms, m.p. 112°–113°, $[\alpha]_D + 72°$ (c, 0.9).

EXAMPLE 13

3α-Hydroxy-21-[2'-(N-methylpiperazino)ethoxy]-5α-pregnane-11,20-dione

A solution of 21-(2'-chloroethoxy)-3α-hydroxy-5α-pregnane-11,20-dione 3-nitrate (0.5 g.) in N-methylpiperazine (10 ml.) was heated on a steam bath for 2 hours, cooled and partitioned between water and ether. The organic layer was washed with water, dried ($Na_2SO_4$) and evaporated.

A solution of the residue, crude 3α-hydroxy-21-[2'-(N-methylpiperazino)ethoxy]-5α-pregnane-11,20-dione 3-nitrate (0.25 g.), in acetic acid (10 ml.) was treated with powdered zinc (1.0 g.) at room temperature for 45 minutes. The zinc was removed by filtration and washed with acetic acid. The filtrate and washings were poured into water, neutralised with 40% aqueous sodium hydroxide and extracted with ether. The extract was washed with water, dried ($Na_2SO_4$) and evaporated. The residue was subjected to preparative t.l.c. ($EtOAc/CHCl_3/(CH_3)_2CO$, , 1:1:3), to give title compound (0.2 g.) as a white foam, $[\alpha]_D + 33°$ (c, 3.0).

EXAMPLE 14

3α-Hydroxy-21-methoxy-5β-pregnane-11,20-dione

Freshly prepared silver oxide (690 mg.) was added to a solution of 3α-acetoxy-21-hydroxy-5β-pregnane-11,20-dione (68.3 mg.) in methyl iodide (1.5 ml.) and the resulting mixture was refluxed for 1 hour, allowed to stand overnight and then refluxed for a further 3 hours. The reaction was partitioned between water and chloroform and the chloroform layer was washed with water, dried ($Na_2SO_4$) and evaporated to give 3α-acetoxy-21-methoxy-5β-pregnane-11,20-dione (69 mg.) as a foam. This was dissolved in methanol (1.25 ml.) and refluxed with 10% aqueous potassium bicarbonate solution (0.6 ml.) for 2.5 hours. The reaction mixture was allowed to cool and was partitioned between water and ether. The ether layer was washed with water, dried ($Na_2SO_4$) and evaporated. The product was purified by preparative t.l.c. (ethyl acetate:chloroform; 1:1) to give the title compound as a foam, $[\alpha]_D + 80°$, (c 2.36).

EXAMPLE 15

21-(2'-Cyanoethoxy)-3α-hydroxy-5α-pregnane-11,20-dione a. A solution of 20β,21-epoxy-3α-hydroxy-5α-pregnan-11-one 3-nitrate (1.0 g.) in ether (40 ml.) was treated with ethylene cyanohydrin (10 ml.) and boron trifluoride diethyl etherate (10 drops) at room temperature for 2 hours. The mixture was then partitioned between water and ether and the organic layer was washed with water, dried ($Na_2SO_4$) and evaporated.

The residue, crude 21-(2'-cyanoethoxy)-3α,20β-dihydroxy-5α-pregnan-11-one 3-nitrate (1.3 g.) was dissolved in acetone (50 ml.), treated with Jones' reagent (1 ml.) at room temperature for 5 minutes and poured into water. The precipitated solid was collected by filtration, washed with water and dissolved in chloroform. The resulting solution was dried ($Na_2SO_4$) and evaporated.

The less polar product, crude 21-(2'-cyanoethoxy)-3α-hydroxy-5α-pregnan-11-one 3-nitrate (0.3 g.) was dissolved in acetic acid (8.0 ml.) and treated with powered zinc (0.8 g.) at room temperature for 30 minutes. The zinc was then removed by filtration and washed with acetic acid. The filtrate and washings were poured into water, neutralised with 40% aqueous sodium hydroxide and extracted with ether. The extract was washed with water, dried ($MgSO_4$) and evaporated to give title compound (0.2 g.) as a white foam, $[\alpha]_D + 87°$ (c 1.4).

b. A solution of 20β, 21-epoxy-3α-hydroxy-5α-pregnan-11-one (1.0 g.) in ether (40 ml.) was treated with ethylene cyanohydrin (10 ml.) and boron trifluoride diethyl etherate (10 drops) at room temperature for 2 hours. The mixture was then partitioned between water and ether and the organic layer was washed with water, dried ($Na_2SO_4$) and evaporated. The residue, crude 21-(2'-cyanoethoxy)-3α,20β-dihydroxy-5α-pregnan-11-one (0.83 g.) was dissolved in acetone (60 ml.) and treated with Jones' reagent (1.2 ml.) at room temperature for 5 minutes. The mixture was then partitioned between water and ether and the organic layer was washed with water, dried ($Na_2SO_4$) and evaporated.

The product, crude 21-(2'-cyanoethoxy)-5α-pregnane-3,11,20-trione (0;80 g.) was treated with chloroiridic acid solution (24 ml.). The mixture was refluxed for 24 hours cooled and partitioned between water and ether. The organic layer was washed with saturated aqueous sodium bicarbonate, water, dried ($Na_2SO_4$) and evaporated. The residue was subjected to preparative t.l.c. EtOAc, petrol (1:1) to give title compound (0.2 g.) as a white foam, $[\alpha]_D + 85°$ (c 1.1).

EXAMPLE 16

21-[2'-(Ethoxycarbonyl)ethoxy]-3α-hydroxy-5α-pregnane-11,20-dione

A solution of 21-(2'-cyanoethoxy)-3α-hydroxy-5α-pregnane-11,20-dione (0.25 g.) in ethanol (10 ml.) was treated with dry hydrogen chloride at room temperature for 2 hours. The solution was then partitioned between water and ether and the organic layer was washed with water, dried ($Na_2SO_4$) and evaporated. The residue was subjected to preparative t.l.c. EtOAc/petrol 2:1 to give title compound (0.093 g.) as an oil; $[\alpha]_D + 57°$ (c 1.2).

EXAMPLE 17

21-(2'-Chloroethoxy)-3α-hydroxy-5α-pregnane-11,20-dione

A solution of 20β,21-epoxy-3α-hydroxy-5α-pregnan-11-one (1.0 g.) in ethylene chlorohydrin (25 ml.) was treated with boron trifluoride diethyletherate (3 drops) at room temperature for 1½ hours. The solution was then partitioned between water and ether and the organic layer was washed with water, dried ($Na_2SO_4$) and evaporated. The more polar product, crude 21-(2'-chloroethoxy)-3α,20β-dihydroxy-5α-pregnan-11-one (1.3 g.) was dissolved in acetone (98 ml.) and treated with Jones' reagent (1.8 ml) at 0° for 5 minutes. The resulting mixture was partitioned between water and ether and the organic layer was washed with water, dried ($Na_2SO_4$) and evaporated. The less polar product, crude 21-(2'-chloroethoxy)-5α-pregnane-3,11,20-trione (1.2 g.) was treated with 'stock' chloroiridic acid solution (36 ml.). The resulting solution was refluxed for 24 hours, cooled and partitioned between water and ether. The organic layer was washed with saturated aqueous sodium bicarbonate and water, dried ($Na_2SO_4$) and evaporated. The residue was subjected to preparative t.l.c. EtOAc/petrol 1:1, to give title compound (0.674 g.) as a white foam; $[\alpha]_D + 62°$ (c 0.9).

EXAMPLE 18

21-(3'-Chloropropoxy)-3α-hydroxy-5α-pregnane-11,20-dione

A solution of 20β,21-epoxy-3α-hydroxy-5α-pregnan-11-one (1.0 g.) in 3-chloropropanol (5 ml.) was treated with boron trifluoride diethyl etherate (6 drops) at room temperature for 5 hours. A further quantity of boron trifluoride diethyl etherate (6 drops) was added and the mixture was left at room temperature for a further 1½ hours. The mixture was then poured into water and the gummy precipitate was collected by filtration and washed with water. A solution of the precipitate in chloroform was dried ($Na_2SO_4$) and evaporated.

The more polar product, crude 21-(3'-chloropropoxy)-3α,20β-dihydroxy-5α-pregnan-11-one (1.25 g.) was dissolved in acetone (63 ml.) and treated with Jones' reagent (1.4 ml.) at room temperature for 5 minutes. The mixture was partitioned between water and ether and the organic layer was washed with water, dried ($Na_2SO_4$) and evaporated.

The less polar residue, crude 21-(3'-chloropropoxy)-5α-pregnane-3,11,20-trione (1.1 g.) was treated with 'stock' chloroiridic acid solution. The mixture was then refluxed for 24 hours, cooled and partitioned between water and ether. The organic layer was washed with water, dried ($Na_2SO_4$) and evaporated. The residue was subjected to preparative t.l.c. EtOAc/petrol 1:1 to give title compound (0.54 g.) as a white foam, $[\alpha]_D + 73°$ (c 1.3).

EXAMPLE 19

21-Benzyloxy-3α-hydroxy-5α-pregnane-11,20-dione

A solution of 20β,21-epoxy-3α-hydroxy-5α-pregnan-11-one (0.75 g.) in benzyl alcohol (20 ml.) was treated with boron trifluoride diethyl etherate (0.3 ml.) at room temperature for 24 hours. The solution was then partitioned between water and ether and the organic layer was washed with water, dried ($Na_2SO_4$) and evaporated.

A solution of the residue, crude 21-benzyloxy-3α,20β-dihydroxy-5α-pregnan-11-one in acetone (20 ml.) was treated with excess of Jones' reagent (ca. 1.7 ml.). The mixture was then partitioned between water and ether and the organic layer was washed with water, dried ($Na_2SO_4$) and evaporated. The residue was purified by preparative t.l.c. EtOAc/petrol 1:1 to give 21-benzyloxy-5α-pregnane-3,11,20-trione as white foam which was treated with 'stock' chloroiridic acid solution (30 ml.). The resulting solution was refluxed for 16 hours, cooled and partitioned between water and ether. The organic layer was washed with water, dried ($Na_2SO_4$) and evaporated. The residue was subjected to preparative t.l.c. ($CHCl_3$) to give title compound (0.2 g.); $[\alpha]_D + 70°$ (c 1.4); $\lambda_{inf.}$ 230 nm. ($\epsilon$ 900).

EXAMPLE 20

21-Cyclopentyloxy-3α-hydroxy-5α-pregnane-11,20-dione

A solution of 20β,21-epoxy-3α-hydroxy-5α-pregnan-11-one (0.75 g.) in cyclopentanol (20 ml.) was treated with boron trifluoride diethyl etherate (0.3 ml.) at room temperature for 24 hours. The solution was then partitioned between water and ether and the organic layer was washed with water, dried ($Na_2SO_4$) and evaporated.

A solution of the residue, crude 21-cyclopentyloxy-3α,20β-dihydroxy-5α-pregnan-11-one in acetone (20 ml.) was treated with a slight excess of Jones' reagent (ca. 1.8 ml.). The mixture was then partitioned between water and ether and the organic layer was washed with water, dried ($Na_2SO_4$) and evaporated. The residue was purified by preparative t.l.c. EtOAc/petrol 1:1, to give 21-cyclopentyloxy-5α-pregnane-3,11,20-trione as a white foam. This was treated with 'stock' chloroiridic acid solution (30 ml.). The resulting solution was refluxed for 16 hours, cooled and partitioned between water and ether. The organic layer was washed with water, dried ($Na_2SO_4$) and evaporated. The residue was subjected to preparative t.l.c. ($CHCl_3$) to give title compound (0.3 g.); $[\alpha]_D + 80°$ (c 1.1).

Pharmaceutical Example A 0.04 g. of 21-propoxy-3α-hydroxy-5α-pregnane-11,20-dione were dissolved in 2 ml. of acetone at 20°C. The resultant solution was added to 1 g. of Cremopher EL at 20°C and it was stirred until homogeneous. The acetone was removed by a vigorous stream of nitrogen. The solution was diluted with sterile distilled water containing 0.0125 g. of sodium chloride to give a final volume of 5 ml.

Pharmaceutical Example B 0.045 g. of 3α-hydroxy-5α-pregnane-11,20-dione and 0.015 g. of 21-propoxy-3α-hydroxy-5α-pregnane-11,20-dione were dissolved in 2 ml. of acetone at 20°C. The resultant solution was added to 1 g. of Cremopher EL at 20°C and stirred until homogeneous. The solution was diluted with sterile distilled water containing 0.0125 g. of sodium chloride to give a final volume of 5 ml.

We claim:

1. A compound of the formula:

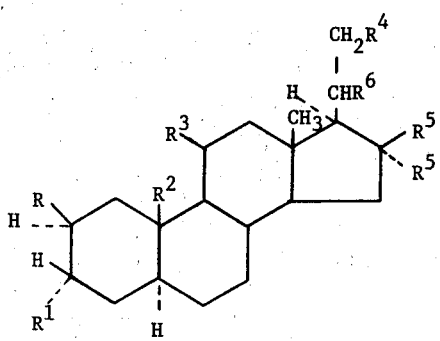

wherein:
R is hydrogen, halogen, $C_1$–$C_6$ alkanoyloxy, $C_1$–$C_6$ alkoxy, $C_1$–$C_6$ alkylthio, $C_1$–$C_5$ alkyl or thiocyanato;

$R^1$ is a hydroxy group, nitro-oxy group, $C_{1-5}$ alkanoyloxy group or $C_{1-5}$ alkanoyloxy group substituted by at least one halogen atom or carboxy or amino group;

$R^2$ is hydrogen or methyl;

$R^3$ is oxygen or

;

$R^4$ is chlorine, bromine or iodine atom, a p-toluene sulphonyloxy or methanesulphonyloxy group or a $C_{1-6}$ alkoxy, $C_{5-6}$ cycloalkoxy, phenyl $C_{1-6}$ alkoxy or phenoxy group or such a hydrocarbyloxy group substituted by at least one halogen atom or carboxyl, $C_{1-6}$ alkoxy carbonyl, $C_{1-6}$-alkoxy or cyano group;

$R^5$ is hydrogen or $C_1$–$C_6$ alkyl $R^6$ is hydroxy or $R^4$ and $R^6$ together are —O— to form an epoxy group joining the 20- and 21- positions.

2. The compound of claim 1 which is 20β,21-epoxy-3α-hydroxy-5α-pregnan-11-one.

3. The compound of claim 1 which is 20β,21-epoxy-3α-hydroxy-16α-methyl-5α-pregnan-11-one.

4. The compound of claim 1 which is 20β,21-epoxy-3α-hydroxy-5α-pregnane.

* * * * *